(12) United States Patent
Meijer et al.

(10) Patent No.: US 8,431,583 B2
(45) Date of Patent: Apr. 30, 2013

(54) USE OF PURINE DERIVATIVES FOR THE MANUFACTURE OF A MEDICAMENT

(75) Inventors: Laurent Meijer, Roscoff (FR); Karima Bettayeb, Roscoff (FR); Hervé Galons, Paris (FR); Nassima Oumata, Paris (FR); Christian Berthou, Brest (FR); Karine Lester, Quimper (FR)

(73) Assignees: Centre National de la Recherche Scientifique, Paris (FR); Universite de Rennes 1, Rennes (FR); Universite Paris Descartes, Paris (FR); Universite de Bretagne Occidentale, Brest (FR); Centre Hospitalier Universitaire de Brest, Brest (FR)

( * ) Notice: Subject to any disclaimer, the term of this patent is extended or adjusted under 35 U.S.C. 154(b) by 242 days.

(21) Appl. No.: 12/675,945

(22) PCT Filed: Sep. 12, 2008

(86) PCT No.: PCT/FR2008/001278
§ 371 (c)(1),
(2), (4) Date: May 13, 2010

(87) PCT Pub. No.: WO2009/068761
PCT Pub. Date: Jun. 4, 2009

(65) Prior Publication Data
US 2010/0311768 A1 Dec. 9, 2010

(30) Foreign Application Priority Data
Sep. 12, 2007 (FR) ..................... 07 06390

(51) Int. Cl.
*C07D 473/16* (2006.01)
*A61P 35/02* (2006.01)
*A61P 13/12* (2006.01)

(52) U.S. Cl.
USPC ..................... 514/263.22; 514/263.4; 544/244

(58) Field of Classification Search .................. 544/277; 514/263.4, 263.22
See application file for complete search history.

(56) References Cited

U.S. PATENT DOCUMENTS

| 5,866,702 | A | 2/1999 | Mackman et al. | |
| 6,627,633 | B2 * | 9/2003 | Trova | 514/263.2 |
| 6,812,232 | B2 * | 11/2004 | Trova | 514/263.2 |
| 6,949,559 | B2 * | 9/2005 | Trova | 514/263.2 |
| 6,969,720 | B2 * | 11/2005 | Trova | 514/263.4 |
| 2005/0153991 | A1 | 7/2005 | Gianella-Borradori et al. | |

FOREIGN PATENT DOCUMENTS

| WO | WO 98/05335 A1 | 2/1998 |
| WO | WO 03/002565 A1 | 1/2003 |
| WO | WO 03/022805 A2 | 3/2003 |
| WO | WO 2005/002584 A1 | 1/2005 |
| WO | WO 2009/068761 A2 | 6/2009 |

OTHER PUBLICATIONS

Wikipedia, "B-cell chronic lymphocytic leukemia", http://en.wikipedia.org/wiki/B-cell_chronic_lymphocytic_leukemia downloaded from the internet May 15, 2012.*
Robak, "Application of New Drugs in Chronic Lymphocytic Leukemia" Medit J Hemat Infect Dis 2010, 2(2): e2010011, DOI 10.4084/MJHID.2010.011 (May 10, 2010).*
Show et al., "Synthesis and Activity of 2,6,9-Trisubstituted Purines," Bioorganic & Medical Chemistry Letters, vol. 7, No. 21, pp. 2697-2702 (1997).
Vesely et al., "Inhibition of Cyclin-Dependent Kinases by Purine Analogues," Eur. J. Biochem., vol. 224, pp. 771-786 (1994).
Nov. 19, 2009 International Search Report issued in International Application No. PCT/FR2008/001278 (with translation).
European Office Action dated Jul. 4, 2011 issued in European Patent Application No. 08 855 583.4.
European Office Action dated Jan. 25, 2012 issued in European Patent Application No. 08 855 583.4.
European Office Action dated Aug. 27, 2012 issued in European Patent Application No. 08 855 583.4.
Nov. 19, 2009 International Preliminary Report on Patentability issued in International Patent Application No. PCT/FR2008/001278 (with translation).

* cited by examiner

*Primary Examiner* — Mark Berch
(74) *Attorney, Agent, or Firm* — Oliff & Berridge, PLC

(57) ABSTRACT

At least one compound of following formula I:

Formula I

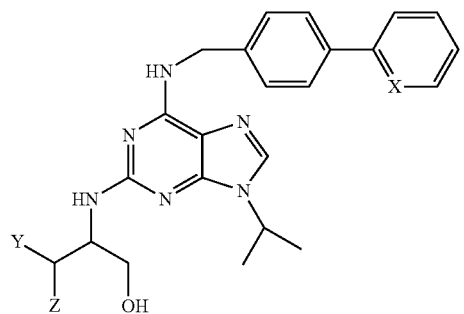

in which:
X is C or N,
Y is $CH_3$ or OH, and
Z is H or $CH_3$,
or one of its pharmaceutically acceptable salts, hydrates, esters or isomers, for use in the manufacture of a medicament to treat pathologies in which an imbalance between cell division and apoptosis is involved.

13 Claims, 2 Drawing Sheets

USE OF PURINE DERIVATIVES FOR THE MANUFACTURE OF A MEDICAMENT

BACKGROUND

The invention relates to the use of purine derivatives in the manufacture of a medicament intended for the treatment of pathologies in which an imbalance between cell division and apoptosis is involved and more particularly in which excessive apoptosis is the cause of the pathology.

It also relates to some of these purine derivatives.

The pathologies in which an imbalance between cell division and apoptosis is involved are in particular chronic lymphoid leukemia and kidney diseases, such as polycystic kidney disease.

Chronic lymphoid leukemia, CLL, is a heterogeneous group of diseases characterized by the accumulation of CD5+ monoclonal B cells in the blood, bone marrow and hematopoietic organs.

It is a disease in which the monoclonal B cells undergo no or little natural apoptosis (cell death) and comprise a small contingent of B cells involved in the cell cycle. In this sense, this disease is a disease rather different from the diseases in which an excessive proliferation, which is not stopped, of the monoclonal cells is observed, in which the monoclonal cells are highly involved in the cell cycle and in which the resistance to apoptosis (cell death) constitutes a phenomenon of secondary pathogenicity.

CLL is commonly classified into separate categories, including B-cell chronic lymphoid leukemia and T-cell chronic lymphoid leukemia. The term "CLL" is commonly understood to mean B-cell chronic lymphoid leukemia (B-CLL).

B-cell chronic lymphoid leukemia, known as B-CLL, is a disease of the B lymphocyte responsible for the accumulation of B lymphocytes of lymphocytic morphology, expressing membrane antigens characteristic of the disease, such as the CD5 and CD23 molecules, in the blood, causing hyperlymphocytosis, in the bone marrow, causing bone marrow failure, and in the lymph nodes, causing polyadenopathy.

B-CLL has been characterized as a single biological entity with a variable progressive nature.

The Binet prognosis classification makes it possible to arrange the profile of progression of the disease into three stages A, B and C.

Among the subjects in stage A of the disease, 41% will progress towards stages B and C. Among the biological parameters, the lymphocyte doubling time of less than 6 months, a rise in the level of soluble CD23 or a rise in the activity of serum thymidine kinase are considered as indicating poor prognosis. The fully identified genetic parameters of poor prognosis include the unmutated forms of the disease (immunoglobulin heavy chain gene in the germinal position on 14q32), deletion abnormalities of the 11q and 17p chromosomes or additional chromosomal abnormalities of 12q+ type. The patients who are carriers of B-CLL and who express these biological characters have a short progression time: thus, 50% of the unmutated patients have progressed in 24 months; 50% of the patients exhibiting a 17p−, an 11q− or a 12q+ have progressed at 15 months. If patients of stage A express these biological criteria for seriousness, the patients of stage B and C should benefit from an active therapeutic attitude.

Although current treatments bring about remissions of the disease, all the patients relapse and there currently exists a consensus in stating that CLL remains an incurable disease.

The real question which is posed today is that of defining, in stage A of the disease, the patients who exhibit a biological potential to progress to a serious state.

The best first-line treatment for B-CLL remains to be defined.

Purine analogs, in particular fludarabine, remain by far the most studied in B-CLL. Fludarabine alone induces a better overall level of response than the use of multidrug therapies comprising alkylating agents and a corticotherapy. Fludarabine induces more complete hematologic remission (7 to 40%) than multidrug therapies of CHOP or CAP (chloraminophene) type.

Despite the better response observed with fludarabine, the benefit observed with regard to overall survival remains marginal. Current therapeutic endeavors are directed at the combinations of fludarabine with conventional chemotherapy, for example fludarabine plus cyclophosphamide, in particular in the resistant forms of the disease. Life expectancy is only 12 months in patients resistant to fludarabine. Nevertheless, the toxicity of the treatment, in particular hematologic toxicity, is increased with these combinations.

Infection is observed in 50% of the patients treated with a combination of fludarabine and cyclophosphamide. Documented sepsis or pneumopathy is observed during the treatment in 25% of the patients treated, undocumented fever and/or hospitalization in 25% of the others.

A therapeutic revolution was achieved by the advent of therapeutic antibodies. In B-CLL, two therapeutic antibodies have emerged: rituximab and alemtuzumab. In B-CLL, the activity of rituximab is handicapped by the low expression of the target, the CD20 antigen, on the B lymphocyte of CLL. Rituximab is deployed in B-CLL in synergy with purine analogs and/or cyclophosphamide (overall response of 59% observed with the fludarabine/cyclophosphamide/rituximab combination in patients resistant to fludarabine, including only 5% of complete response).

The activity of alemtuzumab, directed against an antigen expressed on the leukocytes and the leukemic B lymphocytes of CLL, with a very heterogeneous membrane density of the antigen, is handicapped by its high immunosuppressive activity and the high incidence of reactivations of cytomegalic infections and opportunist infections during or after treatment: the antibody exhibits a high T immunosuppressive activity. The hematologic response to alemtuzumab is 33%; the antibody is capable of destroying clonal B lymphcytes in the blood and the bone marrow but have little effect in the lymph nodes. These points limit the use of the antibody in this indication. Radioimmunotherapy with anti-CD20 coupled to yytrium-90 (Zevalin) induces a low percentage of remission in B-CLL and is responsible for significant myelosuppression.

U.S. Pat. No. 6,812,232 describes purine analogs similar to those of the invention for their activity in inhibiting cell proliferation. In point of fact, in CLL, excessive cell proliferation has stopped.

Patent application WO2005/002584 provides, for its part, for the use of roscovitine, preferably in its (R) absolute configuration, in the treatment of chronic lymphoid leukemia and more particularly of B-cell chronic lymphoid leukemia.

Roscovitine is a Purine Having the Following Formula:

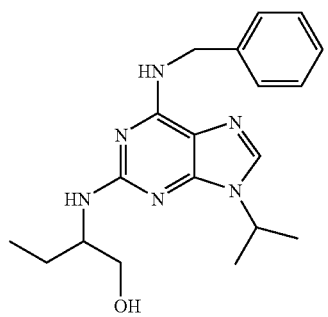 [SMILES: CCC(CO)Nc1nc(NCc2ccccc2)c2ncn(C(C)C)c2n1]

In point of fact, it has now been discovered that roscovitine derivatives have a much higher activity than roscovitine in the treatment of pathologies in which an imbalance between cell division and apoptosis is involved and that they also have, in some cases, a better solubility than roscovitine.

SUMMARY

Thus, the invention provides for the use of at least one compound of following formula I:

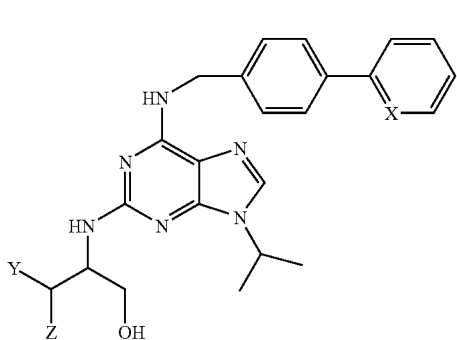

Formula I in which:
X is C or N,
Y is $CH_3$ or OH, and
Z is H or $CH_3$,

DETAILED DESCRIPTION or one of its pharmaceutically acceptable salts, hydrates, esters or isomers,
in the manufacture of a medicament intended to treat pathologies in which an imbalance between cell division and apoptosis is involved.

Figure 1:
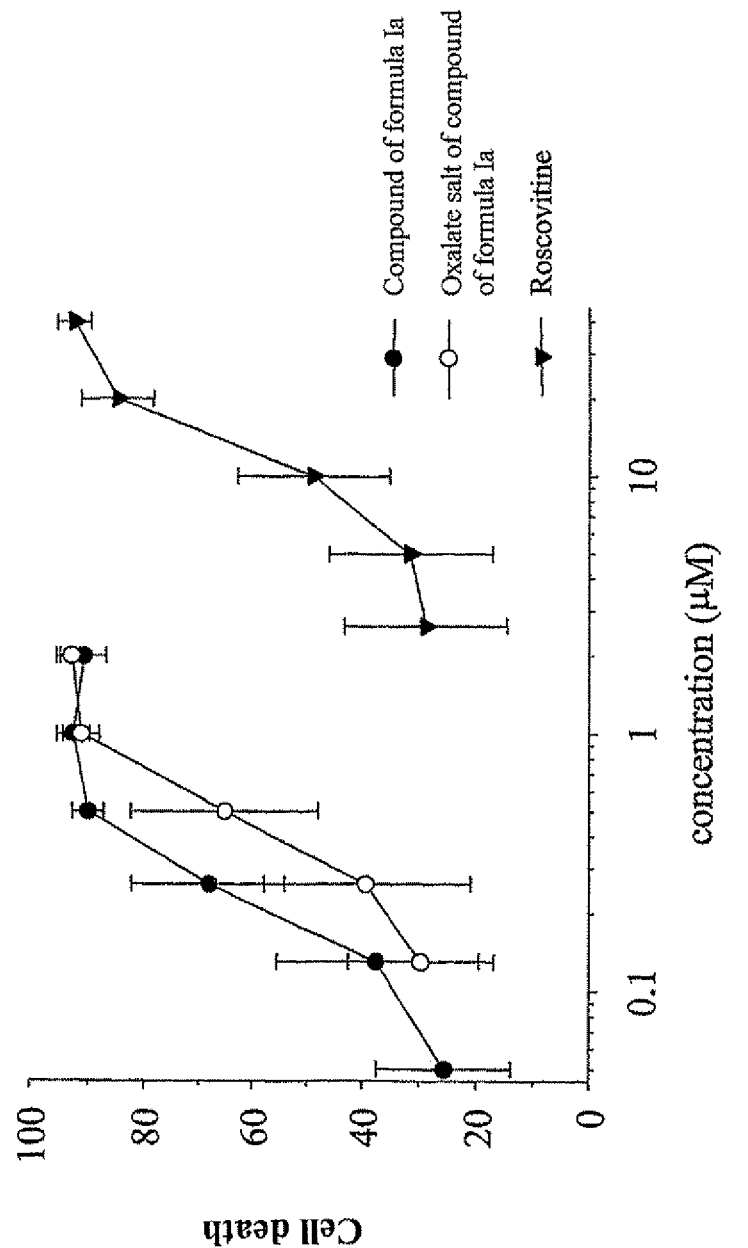
FIG. 1 shows the induction of cell death in chronic lymphoid leukemia cells bu the compound of formula Ia, by the oxalate salt of the compound of formula Ia, and by roscovitine.

FIG. 1 shows the induction of cell death in chronic lymphoid leukemia cells by the compound of formula la, by the oxalate salt of the compound of formula la, and by roscovitine.

In a first alternative form of the invention, the pathology is chronic lymphoid leukemia.

More particularly, the pathology is B-cell chronic lymphoid leukemia.

In a second alternative form of the invention, the pathology is a kidney disease and more particularly polycystic kidney disease.

A preferred salt for use in the manufacture of a medicament for treating pathologies in which an imbalance between cell division and apoptosis is involved is the oxalate salt of the compounds of formula I.

Preferably, the at least one compound used has the following formula I-1, which corresponds to the formula I in which X is N:

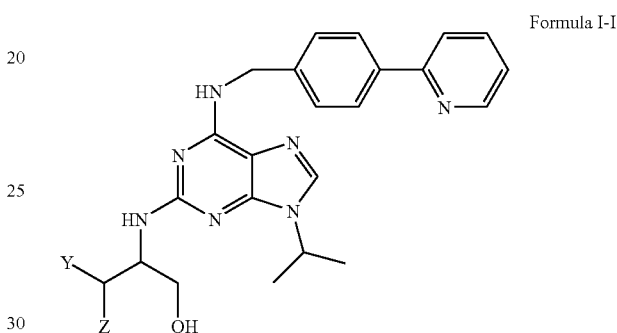

Formula I-I

This is because the compounds are from 4 to 5 times more active in cell models of chronic lymphoid leukemia and polycystic kidney disease and from 5 to 10 times more soluble in an aqueous medium than their correspondants in which X is C, as will be seen below.

However, more preferably, the at least one compound used has the following formula I-II, which corresponds to the formula I in which X is N and Y is OH:

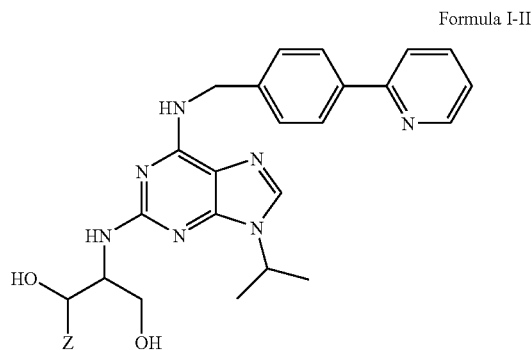

Formula I-II

The compounds with the structure I-II exhibit an activity comparable to that of the I-1 derivatives but their solubility in an aqueous medium is further increased.

More particularly and in a first preferred embodiment, the at least one compound used in the manufacture of a medicament for treating these pathologies is the compound of formula I in which X is N, Y is $CH_3$ and Z is H. This compound has an (R) absolute configuration and has the following formula Ia:

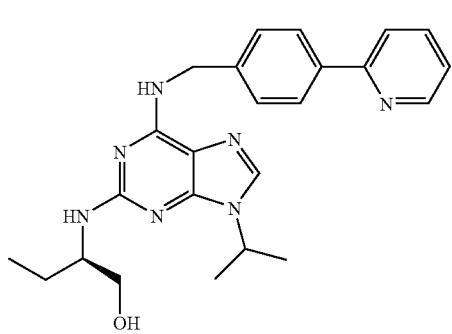

Formula Ia

In a second very particularly preferred embodiment of the invention, the at least one compound has the (S) absolute configuration. This compound has the following formula Ib:

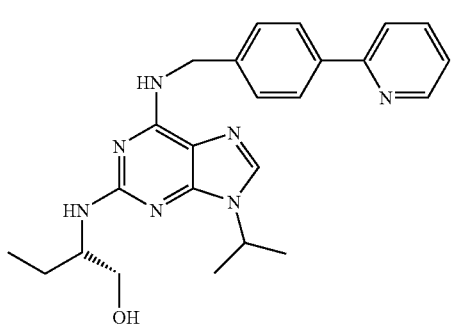

Formula Ib

This is particularly surprising since, in the prior art, it is generally the compounds with the (R) absolute configuration which make it possible to obtain the best results.

In a third very particularly preferred embodiment of the invention, the at least one compound of formula Ia or Ib is in the form of its oxalate salt.

However, in a fourth preferred embodiment of the invention, the at least one compound used in the manufacture of a medicament for treating pathologies in which an imbalance between cell division and apoptosis is involved is the compound of formula I in which X is C, Y is $CH_3$ and Z is H. This compound has the following formula Ic:

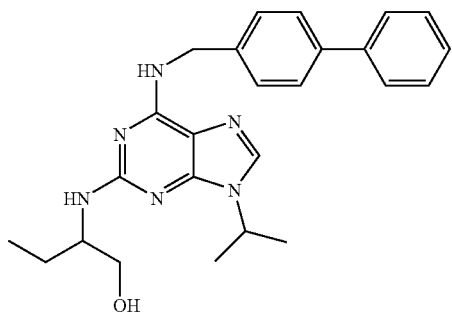

Formula Ic

This compound can be used both in its (S) or (R) absolute configuration and in the form of a mixture of these.

However, in a fifth preferred embodiment of the invention, the at least one compound used is the compound of formula I in which X is N, Y is OH and Z is H. This compound has the following formula Id:

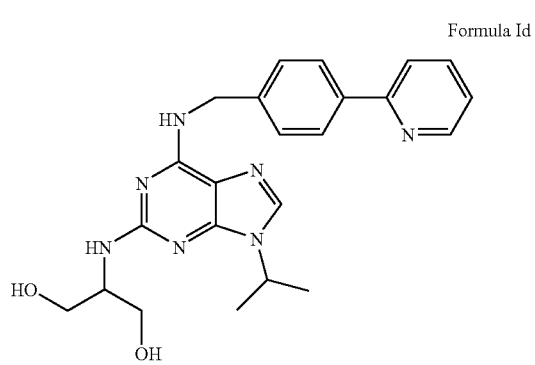 [SMILES: CC(C)n1cnc2c(NCc3ccc(-c4ccccn4)cc3)nc(NC(CO)CO)nc21]

Formula Id

The compound Id can be obtained as described in the following example 1.

EXAMPLE 1

Preparation of the Compound Id

This compound is obtained in 3 stages starting from dichloropurine according to the following scheme:

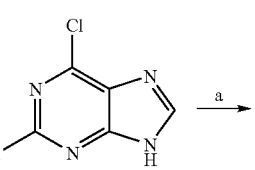

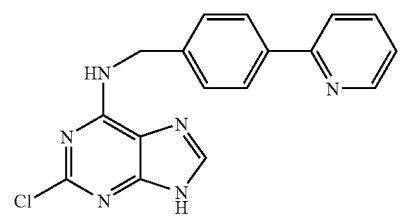

IIIa

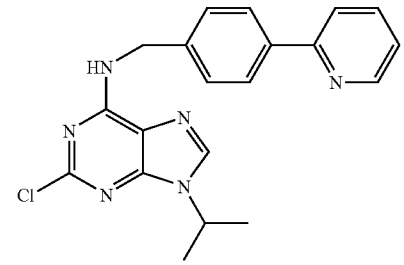

IVa

-continued

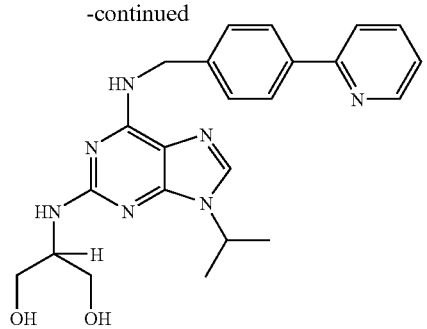

Reactants and Conditions:
a: 4-(2-Pyridyl)benzylamine, n-BuOH, 110° C.; b: 2-bromopropane, K₂CO₃, DMSO; c: serinol, heating 160° C., 8 h).

Stage 1:
2-Chloro-6-[4-(2-pyridyl)phenylmethylamino]-purine (IIIa)

4-(2-Pyridyl)benzylamine (2.0 g, 1.05 mmol) and 3 ml of NEt₃ are added to a solution of 2,6-dichloropurine (2.3 g, 10 mmol) in 20 ml of n-BuOH. After heating at 110° C. for 3 h, the mixture is cooled to 20° C. and the solid is filtered off, washed with 5 ml of cold butanol and then dried under vacuum. Yd=85. M.p. >250° C. ¹H NMR (d₆-DMSO) δ 4.80 (s, 2H, CH₂); 7.20 (m, 1H, H$_{pyridyl}$); 7.45 (d, 2H, H$_{phenyl}$); 7.72 (m, 2H, H$_{pyridyl}$); 7.95 (m, 3H, H$_{phenyl}$ and H-8), 8.54 (d, 1H, J=4.8 Hz, H$_{pyridyl}$).

Stage 2

2-Chloro-9-isopropyl-6-[(4-(2-pyridyl)phenylmethyl-amino]purine (IVa)

K₂CO₃ (3.5 g, 24 mmol) and 1.9 ml (20 mmol) of 2-bromopropane are added to a solution of 2-chloro-6-[4-(2-pyridyl)phenylmethylamino]purine (8 mmol) in 10 ml of DMSO at 18-20° C. After stirring at 18-20° C. for 5 h, 2-bromopropane (0.5 ml) is again added and stirring is continued at 20° C. for 5 h. After adding 50 ml of cold (5° C.) water, the mixture is extracted with EtOAc (3×10 ml) and the organic phases are washed with brine (3×10 ml) and dried over Na₂SO₄. The derivative IVa crystallizes by evaporation of the solvent. It is triturated from 2 ml of 2-propanol and filtered off. Yd 86%. ¹H NMR (CDCl₃): δ 1.58 (d, 6H); 4.79 (hept, 1H); 4.85 (broad s, 2H); 6.59 (broad s, 1H); 7.20-7.23 (m, 1H); 7.49 (d, 2H); 7.73-7.71 (m, 2H); 7.79 (s, 1H); 7.98 (d, 2H); 8.71 (d, 1H).

Stage 3: 2-(1,3-Dihydroxyprop-2-ylamino)-6-[4-(2-pyridyl)phenylmethylamino]-9-isopropylpurine 1d A mixture of the compound IVa (10 mmol) and of serinol (2-aminopropane-1,3-diol) (2 ml) is heated under N₂ at 160° C. for 8 h. After cooling to 20° C., 20 ml of water are added and the mixture is extracted with EtOAc (4×10 ml). The organic solution is washed with 2×20 ml of water, dried and evaporated. The derivative Id crystallizes by triturating from Et₂O.
M.p. 114-117° C. Yd 74%. ¹H NMR (CdCl₃) δ 1.52 (d, 6H); 3.78 (m, 4H); 3.96 (m, 1H); 4.55 (hept, 1H); 4.76 (s, 2H); 5.40 (s, 1H); 6.20 (s, 1H); 7.12 (m, 1H); 7.38 (d, 2H); 7.48 (s, 1H); 7.62 (m, 2H); 7.90 (d, 2H); 8.60 (d, 1H).

In a sixth preferred embodiment of the invention, the at least one compound used is the compound of formula I in which X is N, Y is CH₃ and Z is CH₃. This compound has the following formula Ie:

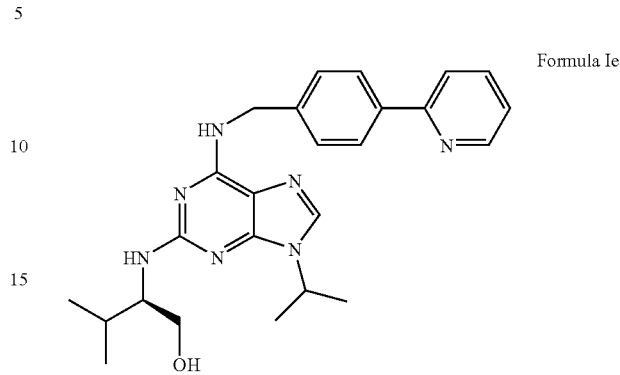

Formula Ie

In a seventh preferred embodiment of the invention, the at least one compound used is the oxalate salt of the compound of formula Ie. This compound has the following formula If:

Formula If

It should be noted that one of the nitrogens of the purine may be involved in the formation of the salt, which corresponds to the combination of one molecule of the purine with the diacid.

In an eighth preferred embodiment of the invention, the at least one compound used is the compound of the following formula Ig:

Formula Ig

This compound is (1R,2R)-2-(1,3-dihydroxybut-2-ylamino)-6-[4-(2-pyridyl)phenylmethylamino]-9-isopropylpurine Ig It is obtained in the same way as the product Id but replacing, in the final stage, aminopropanediol with L-threoninol or (1R,2R)-2-aminobutane-1,3-diol.

It has the following characteristics, measured by NMR:
NMR: 1.2 (d, 3H); 1.4 (d, 6H); 3.70 (m, 4H); 4.10 (m, 1H), 4.52 (hept, 1H); 4.72 (broad s, 2H); 5.50 (s, 1H); 6.2 (broad s, 1H); 7.15 (m, 1H); 7.4 (d, 2H); 7.42 (s, 1H); 7.55 (m, 2H); 7.85 (d, 2H); 8.60 (d, 1H).

In a ninth preferred embodiment of the invention, the at least one compound used is the compound of following formula Ih:

Formula Ih

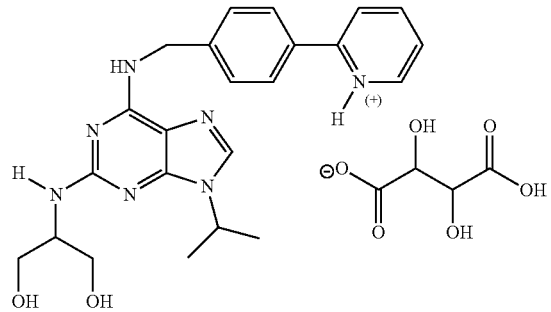

It should be noted that one of the nitrogens of the purine may be involved in the formation of the salt, which corresponds to the combination of one molecule of the purine with the diacid. The three isomers of tartaric acid can be used.

This compound is 2-(1,3-dihydroxyprop-2-ylamino)-6-[4-(2-pyridyl)phenylmethylamino]-9-isopropylpyrine tartrate (Ih).

It is obtained in the following way:

2.1 mmol of tartaric acid, dissolved in isopropanol (1 ml), are added to a solution, brought to 70-80° C., of 2 mmol of Id in solution in isopropanol (1 ml). After cooling, the tartrate of Id is isolated by filtration.

The salts, such as fumarates or hydrochlorides, the hydrates and the esters of the compounds of formulae Ia, Id and Ig and also the isomers of the compounds of formulae Ic and Ig can also advantageously be used.

In particular, the esters of the compounds of formula I also come within the invention.

The preferred esters of the compounds of formula I are acyl esters, such as acetyl esters, nicotinyl esters and esters of amino acids of the L series or D series.

Other preferred esters are formed from amino acids, such as valine or leucine.

The particularly preferred esters have the following formulae II-1 to II-4:

Formula II-1

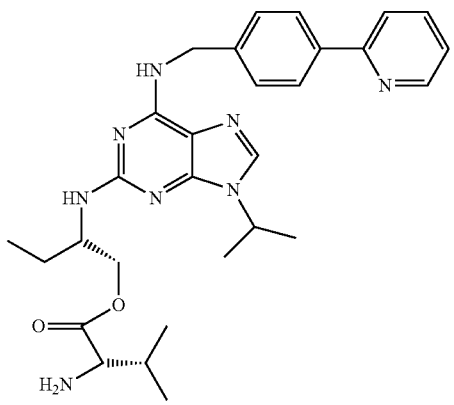

Formula II-2

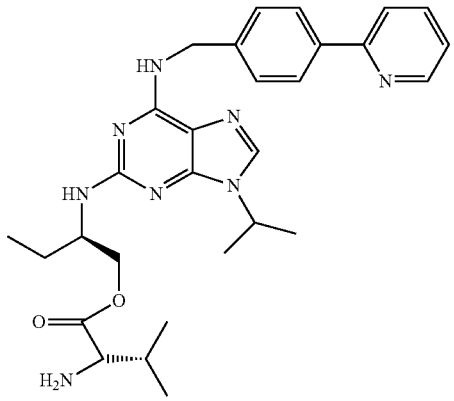

Formula II-3

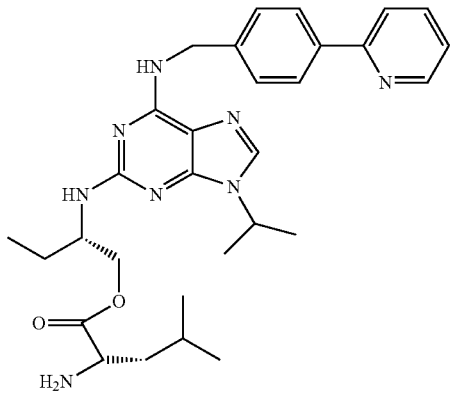

Formula II-4

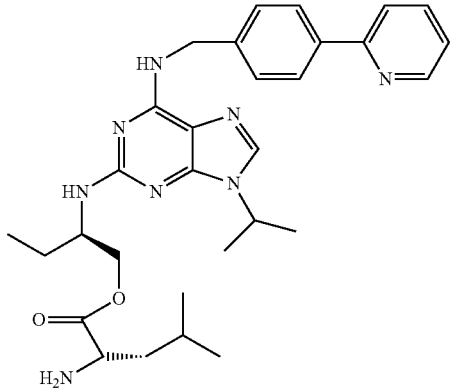

This is because these esters are precursors (prodrugs) of the products of formula I.

Their use in the manufacture of a medicament intended to treat pathologies in which an imbalance between cell division and apoptosis is involved is also a subject matter of the invention.

Figure 2:
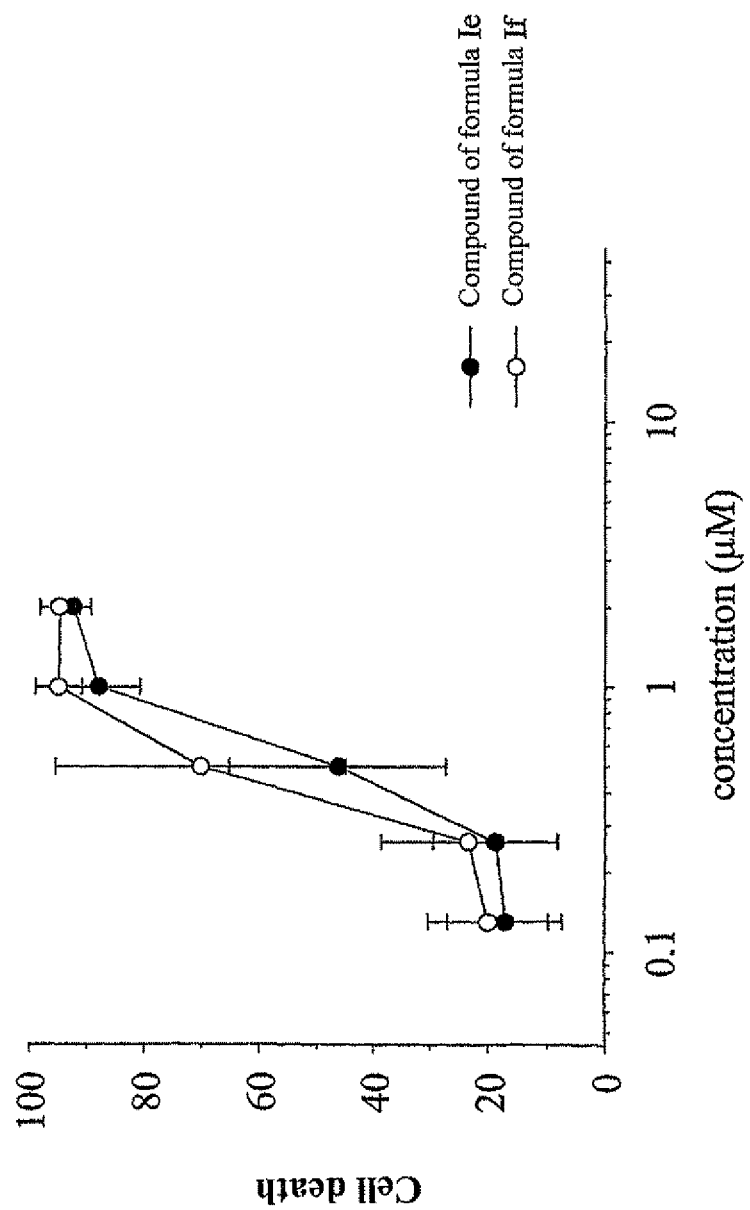
FIG. 2 shows the induction of cell death in chronic lymphoid leukemia cells by the compounds of formulae Ie and If.

A better understanding of the invention will be achieved and other characteristics and advantages of the invention will become more clearly apparent on reading the explanatory description which follows, which is made with reference to the figures, in which:

the appended FIG. 1 shows the induction of cell death by the compound of formula Ia and the oxalate salt of the compound of formula Ia in chronic lymphoid leukemia cells, in comparison with the induction of cell death induced by roscovitine, FIG. 2 shows the induction of cell death by the compounds of formulae Ie and If in chronic lymphoid leukemia cells.

The effects of roscovitine and of the compound of formula Ia and of its oxalate salt were tested at various concentrations in kinase assays.

These tests were carried out as follows:

Buffers buffer A: 10 mM $MgCl_2$, 1 mM EGTA, 1 mM DTT, 25 mM tris-HCl pH 7.5, 50 µg heparin/ml.

buffer C: 60 mM glycerophosphate, 15 mM p-nitrophenyl phosphate, 25 mM MOPS (pH 7.2), 5 mM EGTA, 15 mM $MgCl_2$, 1 mM DTT, 1 mM sodium vanadate, 1 mM phenyl phosphate.

Preparation and Assaying of the Kinases

The kinase activities were assayed in buffer A or C at 30° C. and a final ATP concentration of 15 µM. Controls are carried out with appropriate dilutions of dimethyl sulfoxide.

CDK1/cyclin B (starfish M-phase ovocytes, native) and CDK5/p25 (human, recombinant) were prepared and assayed as described in Leclerc S. et al., J. Biol. Chem., 2001, 276, 251-60. Assaying is carried out with 1 mg histone H1/ml, in the presence of 15 µm $[\gamma\text{-}^{33}P]ATP$ (3000 Ci/mmol; 10 mCi/ml) in a final volume of 30 µl. After incubating at 30° C. for 30 min, 25 µl aliquots of supernatant were deposited on 2.5×3 cm pieces of Whatman P8 phosphocellulose papers and then, 20 sec. later, the filters were washed 5 times in a solution of 10 ml of phosphoric acid/liter. The filters are subsequently counted in the presence of 1 ml of ACS (Amersham).

CDK2/cyclin A and CDK2/cyclin E (human, recombinant, expressed in insect cells) are assayed like CDK1.

CDK9/cyclin T (human, recombinant, expressed in insect cells) is assayed like CDK1/cyclin B, with a pRB fragment (AA773-928) (3.5 µg/assay) as substrate.

GSK-3 α/β (pig brain, native, affinity-purified) is assayed like CDK1/cyclin B but in buffer A and with a specific GSK-3 substrate (GS-1: YRRAAVPPSPSLSRHSSPHQSpEDEEE) (Bach S. et al., J. Biol. Chem., 2005, 280, 31208-19).

CK1δ/e (pig brain, native, affinity-purified) is assayed like CDK1/cyclin B but in buffer A and with a specific substrate, RRKHAAIGSpAYSITA (Reinhardt J. et al., Protein Expr. & Purif., 2007, 54, 101-9).

DYRK1A (human, recombinant, expressed in *E. coli* cells) is assayed like CDK1/cyclin B.

The mean inhibitory concentration $IC_{50}$ values were calculated from the dose/response curves and are listed in µM in the following table I.

TABLE I

| Kinase | (R)-Roscovitine | Compound of formula Ia (R) form | Compound of formula Ib (S) form |
| --- | --- | --- | --- |
| CDK1/cyclin B | 0.33 | 0.09 | 0.15 |
| CDK2/cyclin A | 0.21 | 0.072 | 0.080 |
| CDK2/cyclin E | 0.17 | 0.041 | 0.060 |
| CDK5/p25 | 0.28 | 0.11 | 0.12 |
| CDK7/cyclin H | 0.80 | 1.10 | — |
| CDK9/cyclin T | 0.23 | 0.18 | 0.11 |
| CK1 | 4.00 | 0.40 | 0.61 |
| DYRK1A | 3.00 | 3.60 | 0.9 |
| Erk2 | 11.00 | 3.60 | 2.1 |
| GSK-3α/β | 60.00 | 12.0 | ≧30.00 |

It is seen, from table I, that, for all the protein kinases, the compound of formula Ib of (S) configuration exhibits inhibitory activities for the various kinases which are similar to the activities of roscovitine and which are slightly lower than the activities of the compound of formula Ia, that is to say of its homolog of (R) absolute configuration.

However, when the compound of formula Ia and its oxalate salt and compounds of formulae Ie and If were tested on B chronic lymphoid leukemia cells taken from patients having this type of chronic lymphoid leukemia, it is found that, surprisingly, these compounds have an apoptosis-inducing activity on the CLL cells which is much greater, from 50 to 100 times greater, than the activity of roscovitine, as is seen in FIGS. 1 and 2.

Furthermore, the effect of compounds Ia, Ib, Ic, Id, Ie and If and of the oxalate salt of the compound Ia on the induction of cell death of the B2 lymphocytes originating from patients was compared with the effect of (R)-roscovitine on this same induction.

The B2 lymphocytes are lymphocytes involved in 32-cell chronic lymphoid leukemia.

Cell viability is determined by the reduction of 3-(4,5-dimethylthiazol-2-yl)-5-(3-carboxymethoxyphenyl)-2-(4-sulfophenyl)-2H-tetrazolium (MTS).

Cell death is determined by the measurement of the level of the activity of the lactate dehydrogenase (LDH) released during lysis of the cells. The two processes are described in detail in "Ribas J. and Boix J. Cell differentiation, caspase inhibition, and macromolecular synthesis blockage, but not BCL-2 or BCL-XL proteins protect SH-SY5Y cells from apoptosis triggered by two CDK inhibitory drugs. Exp. Cell Res., 2004, 295, 9-24".

The results obtained are shown in the following table 2:

TABLE 2

| Compound of formula | Induction of cell death |
| --- | --- |
| (R)-Roscovitine | 8.96 |
| Ia | 0.20 |
| Ib | 0.09 |
| Ia oxalate | 0.2 |
| Ic | 1.25 |
| Id | 0.25 |
| Ie | 0.51 |
| If | 0.38 |

In table 2, the values shown are the mean inhibitory concentration $IC_{50}$ values, expressed in µM.

The effect of the compounds Ib and Id of the invention on polycystic kidney disease was also tested on the MUCK line in comparison with (R) roscovitine. The compounds Ib and Id are 50 to 60 times more active than roscovitine.

The solubility of the compounds of the invention in which X is N, it has been said, are 5 to 10 times more soluble in water than those in which X is C.

Thus, the compound of formula Ic, in which X is C, has a solubility in water of 0.5 µg/ml, whereas the corresponding compound in which X is N, that is to say the compound of formula Ib, has a solubility in water of 3.3 µg/ml.

The compounds of formulae Ib to Ih per se are also subject-matters of the invention.

The esters of the compounds of formula I also come within the invention.

The preferred esters of the compounds of formula I are acyl esters, such as acetyl esters, nicotinyl esters and esters of amino acids of the L series or D series.

The preferred esters are formed from amino acids, such as valine or leucine.

The particularly preferred esters have the following formulae II-1 to II-4:

Formula II-1

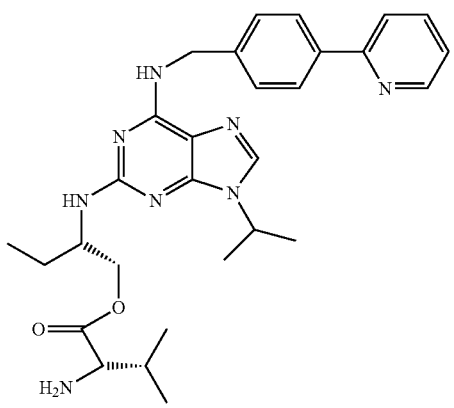

Formula II-2

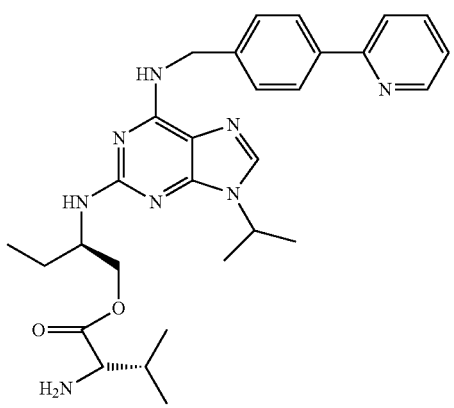

Formula II-3

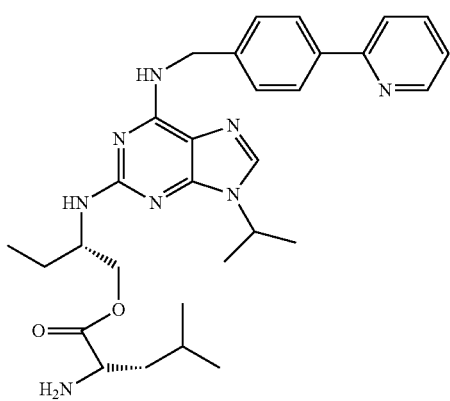

Formula II-4

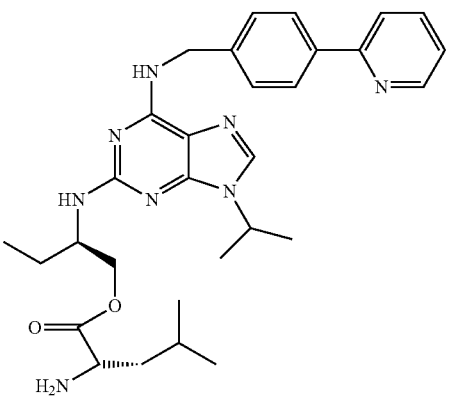

This is because these esters are precursors (prodrugs) of the products of formula I.

Thus, the compounds of the invention are particularly effective for use in the manufacture of a medicament for treating chronic lymphoid leukemia. They are also particularly appropriate for administration in a method for the treatment of patients affected by chronic lymphoid leukemia.

They are also particularly effective for use in the manufacture of a medicament for treating kidney diseases and in particular polycystic kidney diseases. In the same way, they are particularly appropriate for administration in a method for the treatment of patients affected by a kidney disease and in particular by polycystic kidney disease.

A person skilled in the art will easily understand that the compounds of the invention can be used as a mixture with one another, of two or more, and also in combination with other compounds having a therapeutic activity in the treatment of chronic lymphoid leukemia or kidney diseases, such as polycystic kidney disease, and/or in combination with any pharmaceutically acceptable excipient in the manufacture of a medicament and that these combinations and mixtures also come within the invention.

What is claimed is:

1. A method for the treatment of patients affected by chronic lymphoid leukemia, comprising at least one step of administration to said patients of at least one compound of following formula Id:

Formula Id

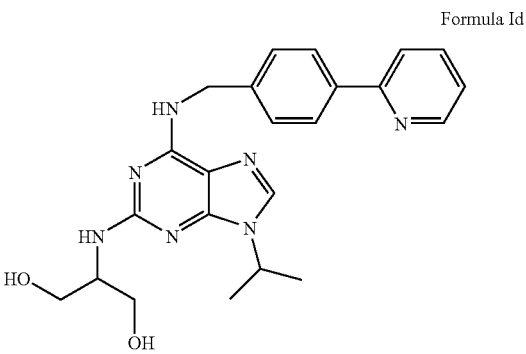 [SMILES: CC(C)n1cnc2c(NCc3ccc(-c4ccccn4)cc3)nc(NC(CO)CO)nc21]

or one of its pharmaceutically acceptable salts or esters, or of following formula Ie:

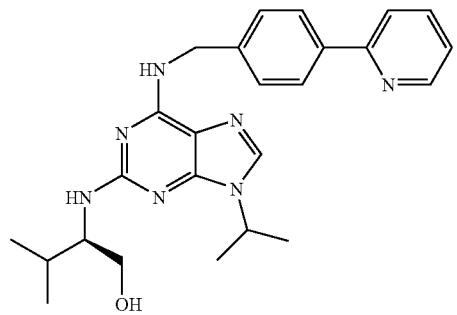
Formula Ie or one of its pharmaceutically acceptable salts or esters, or of an oxalate salt of a compound of following formula If:

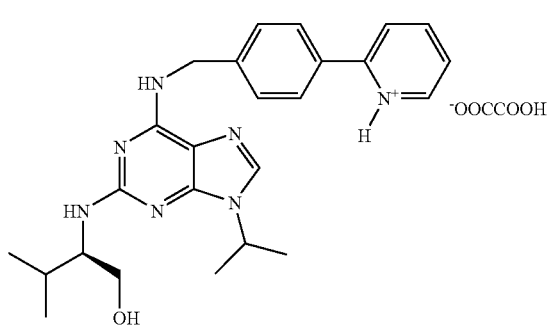
Formula If or of following formula Ig:

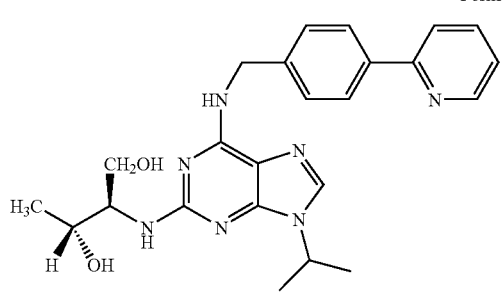
Formula Ig or one of the pharmaceutically acceptable salts, or of following formula Ih:

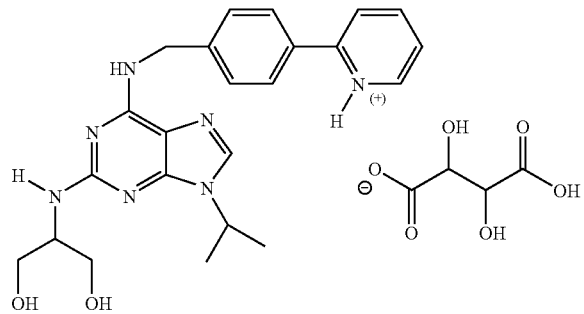
Formula Ih or of following formula Ib:

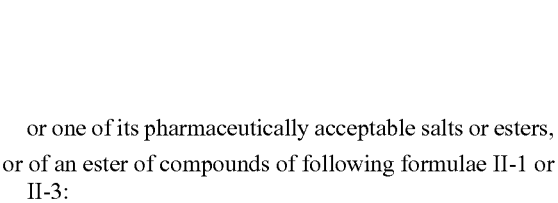
Formula Ib or one of its pharmaceutically acceptable salts or esters, or of an ester of compounds of following formulae II-1 or II-3:

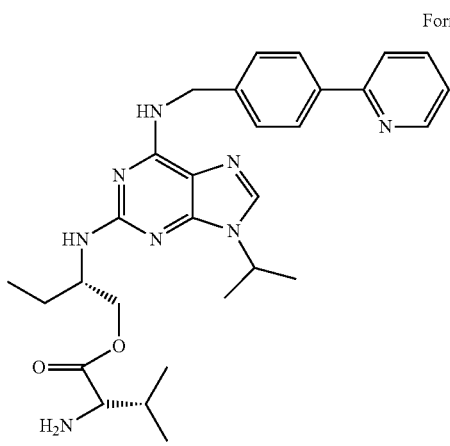
Formula II-1

Formula II-3

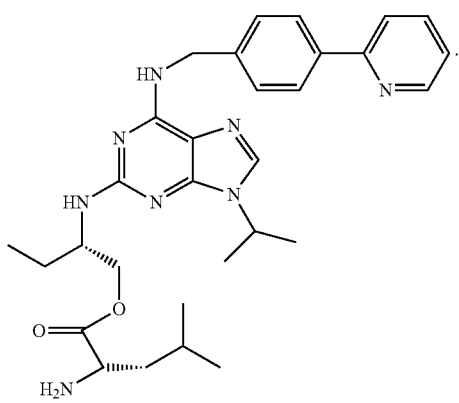

2. The method according to claim 1, wherein the pharmaceutically acceptable salt is an oxalate or tartrate or hydrochloride or fumarate salt.

3. The method according to claim 1, wherein the at least one compound is the compound of following formula Ib:

Formula Ib

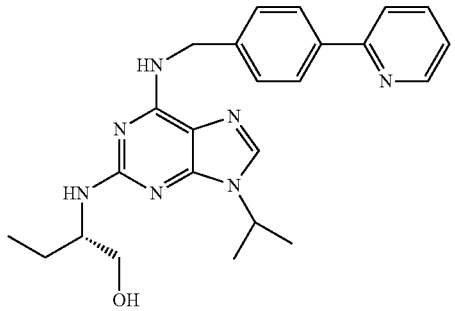

or one of its pharmaceutically acceptable salts or esters.

4. The method according to claim 3, wherein the at least one compound is the oxalate salt of the compound of formula Ib.

5. A method for the treatment of patients affected by polycystic kidney disease, comprising at least one step of administration to said patients of at least one compound of following formula I:

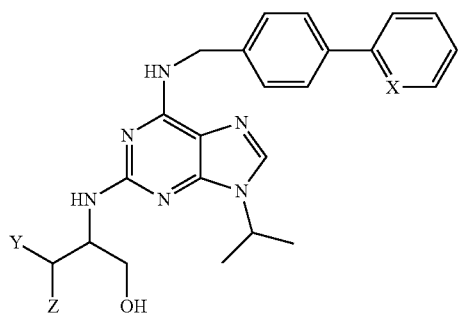

in which:
X is N,
Y is CH$_3$ or OH, and
Z is H or CH$_3$,
or one of its pharmaceutically acceptable salts or esters.

6. The method according to claim 5, wherein the pharmaceutically acceptable salt is an oxalate or tartrate or hydrochloride or fumarate salt.

7. The method according to claim 5, wherein the at least one compound is the compound of formula I in which X is N and Y is OH.

8. The method according to claim 5, wherein the at least one compound is the compound of formula I in which X is N, Y is CH$_3$ and Z is H, of following formula Ia:

Formula Ia

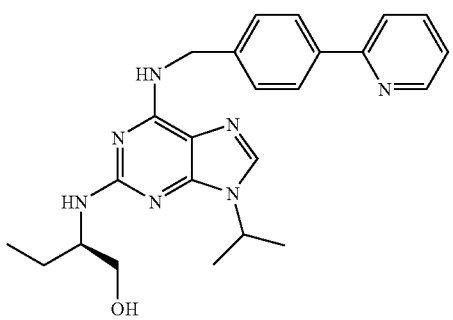

or one of its pharmaceutically acceptable salts or esters, or of formula I in which X is N, Y is OH and Z is H, of following formula Id:

Formula Id

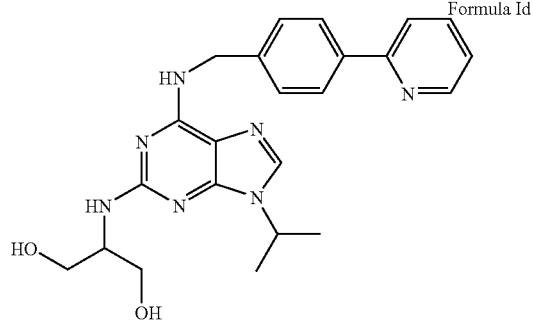 [SMILES: CC(C)n1cnc2c(NCc3ccc(-c4ccccn4)cc3)nc(NC(CO)CO)nc21]

or one of its pharmaceutically acceptable salts or esters, or of formula I in which X is N, Y is CH$_3$ and Z is CH$_3$, of following formula Ie:

Formula Ie

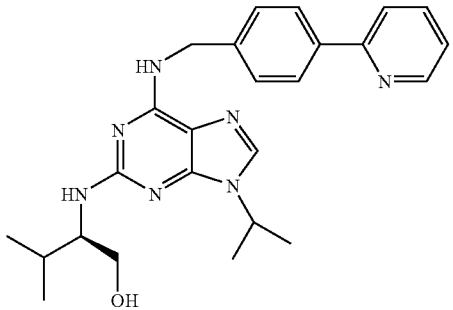

or one of its pharmaceutically acceptable salts or esters, or an oxalate salt of the compound of formula I in which X is N, Y is CH₃ and Z is CH₃, of following formula If:

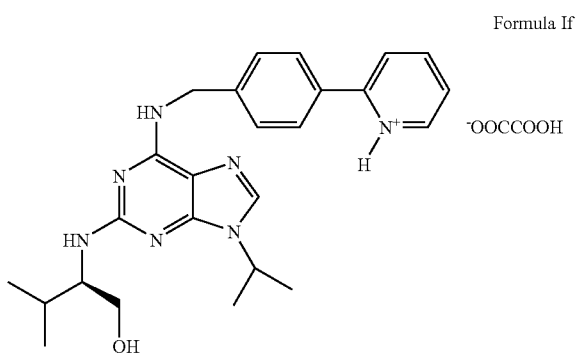

Formula If or has the following formula Ig:

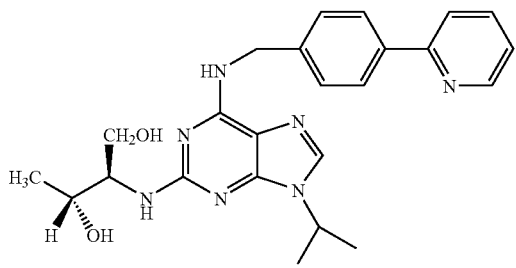

Formula Ig or one of the pharmaceutically acceptable salts,
or has the following formula Ih:

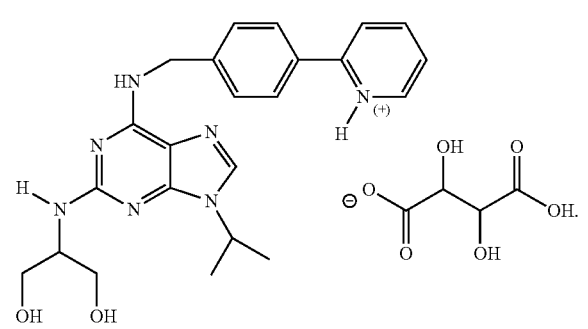

Formula Ih

9. The method according to claim 5, wherein the at least one compound is the compound of formula I in which X is N, Y is CH₃ and Z is H, of (S) absolute configuration, of following formula Ib:

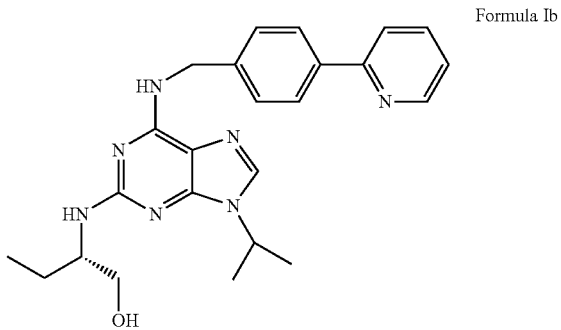 [SMILES: CC[C@@H](CO)Nc1nc(NCc2ccc(-c3ccccn3)cc2)c2ncn(C(C)C)c2n1]

Formula Ib or one of its pharmaceutically acceptable salts or esters.

10. The method according to claim 5, wherein the at least one compound is an ester chosen from the compounds of following formulae II-1 to II-4:

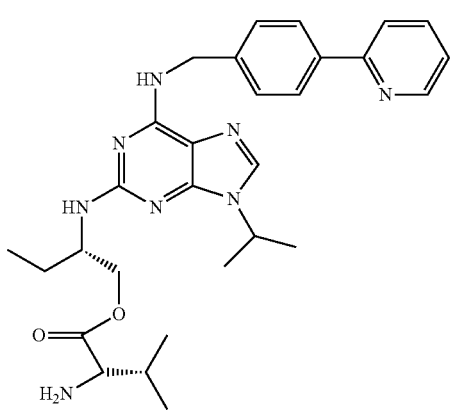

Formula II-1

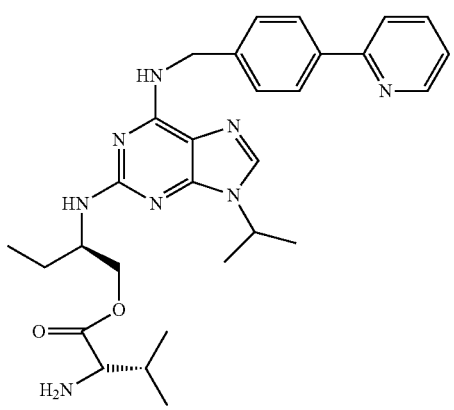

Formula II-2

Formula II-3
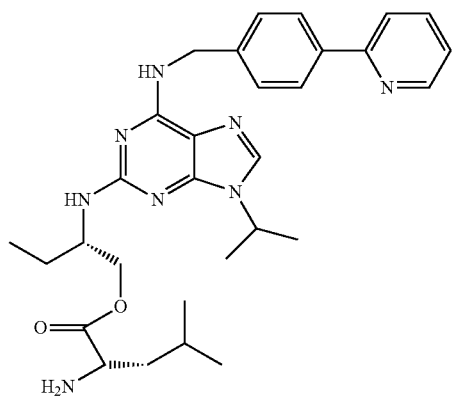
Formula II-4
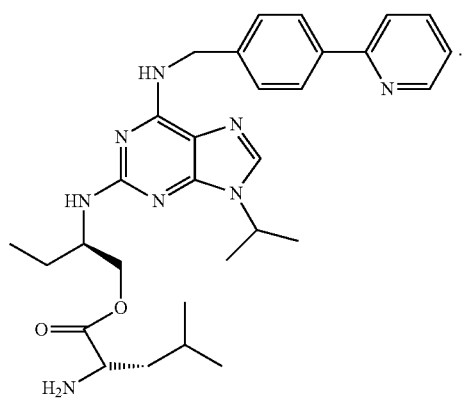
11. The compound of following formula Ib:
Formula Ib
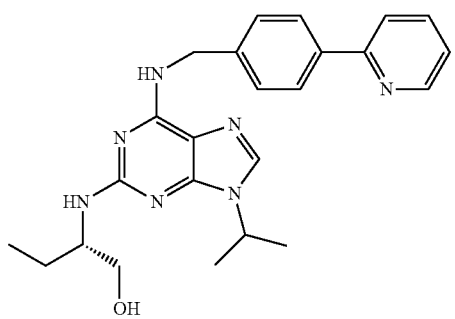
or one of its salts or esters.
12. The compound of following formula Id:
Formula Id
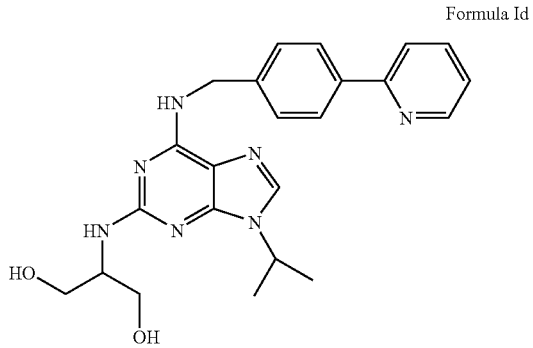 [SMILES: CC(C)n1cnc2c(NCc3ccc(-c4ccccn4)cc3)nc(NC(CO)CO)nc21]
or one of its salts or esters, or
of following formulae Ie:
Formula Ie
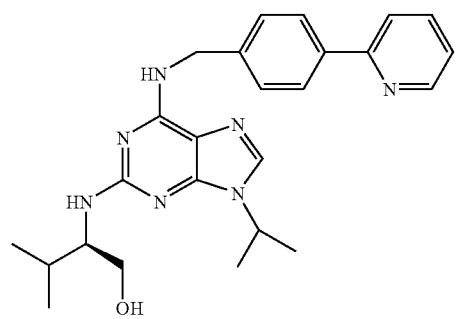
or the salts or esters of the latter, or
of following formula If:
Formula If
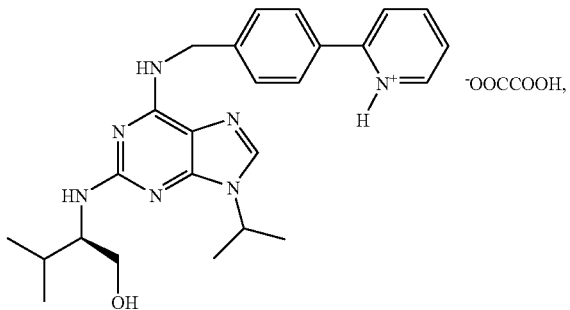

or
of following formula Ig:
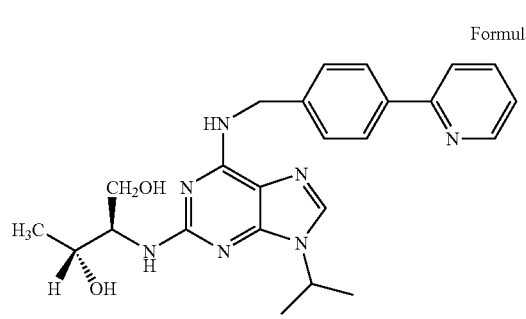
Formula Ig
or one of its salts or esters, or
of following formula Ih:
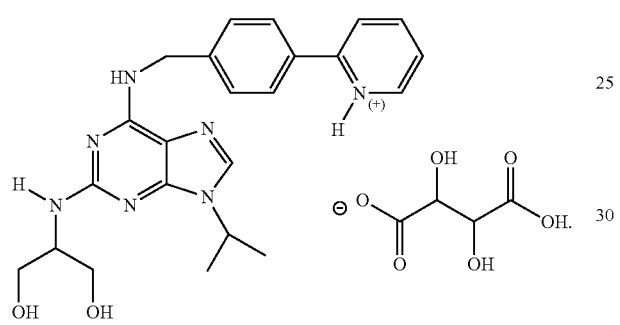
Formula Ih
13. A compound, wherein it has the following formulae II-1 to II-4:
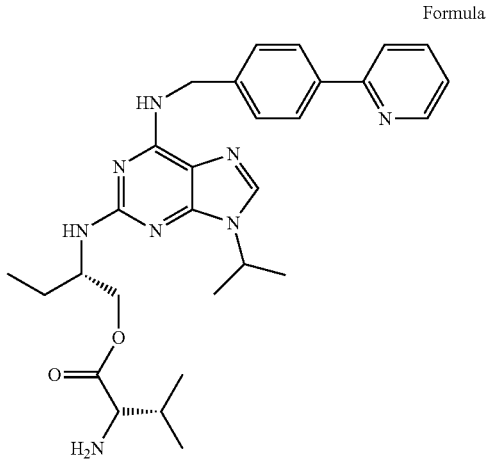
Formula II-1
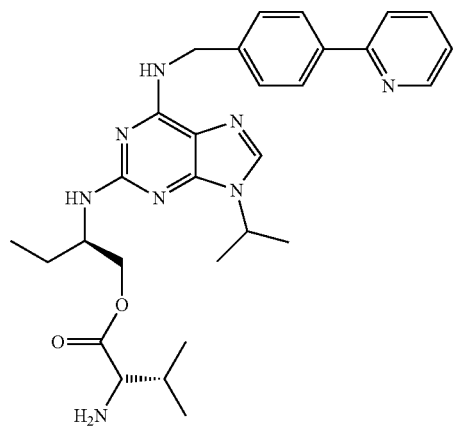
Formula II-2
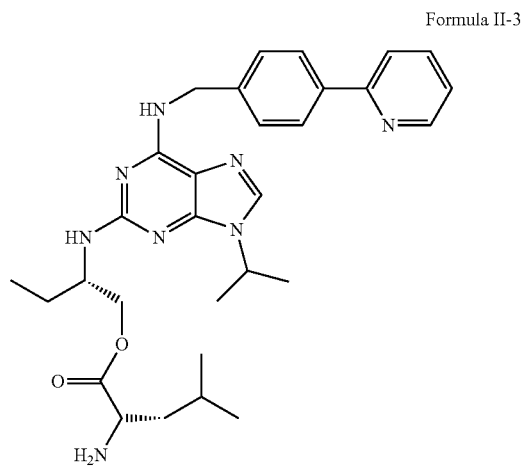
Formula II-3
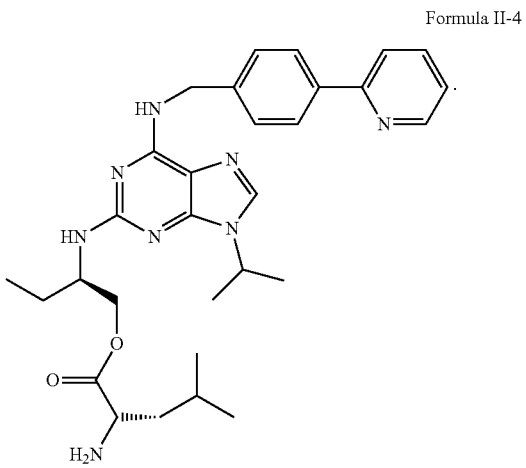
Formula II-4
* * * * *